(12) United States Patent
Brotz

(10) Patent No.: US 6,478,809 B1
(45) Date of Patent: Nov. 12, 2002

(54) SUTURE AND METHOD OF USE

(76) Inventor: Gregory R. Brotz, P.O. Box 1322, Sheboygan, WI (US) 53081

( * ) Notice: Subject to any disclaimer, the term of this patent is extended or adjusted under 35 U.S.C. 154(b) by 0 days.

(21) Appl. No.: 09/911,154

(22) Filed: Jul. 23, 2001

Related U.S. Application Data

(63) Continuation-in-part of application No. 09/498,308, filed on Feb. 4, 2000, now Pat. No. 6,264,675.

(51) Int. Cl.[7] .............................................. A61B 17/04
(52) U.S. Cl. ...................................... 606/228; 606/224
(58) Field of Search ................................ 606/228, 138, 606/151, 214, 215, 216, 223, 224, 232, 229, 231

(56) References Cited

U.S. PATENT DOCUMENTS

| | | | | |
|---|---|---|---|---|
| 3,608,095 A | * | 9/1971 | Barry | 606/224 |
| 3,608,539 A | * | 9/1971 | Miller | 600/567 |
| 3,890,975 A | * | 6/1975 | McGregor | 606/227 |
| 5,180,385 A | * | 1/1993 | Sontag | 606/223 |
| 5,425,746 A | * | 6/1995 | Proto et al. | 606/224 |
| 5,425,747 A | * | 6/1995 | Brotz | 606/215 |
| 5,569,302 A | * | 10/1996 | Proto et al. | 606/228 |
| 5,584,859 A | * | 12/1996 | Brotz | 606/215 |
| 5,928,267 A | * | 7/1999 | Bonutti et al. | 606/215 |
| 5,931,855 A | * | 8/1999 | Buncke | 606/215 |
| 5,989,268 A | * | 11/1999 | Pugsley et al. | 606/144 |
| 6,197,043 B1 | * | 3/2001 | Davidson | 606/228 |

* cited by examiner

Primary Examiner—A. Vanatta
(74) Attorney, Agent, or Firm—William Nitkin

(57) ABSTRACT

A suture member for joining the first and second sides of a cut in body tissue, such suture member having an elongated body member in one embodiment with a needle and thread member disposed at one end thereof and with externally activatable adhesive disposed on the suture member. The adhesive is activated by application of high-frequency radiation directed through the body tissue to retain the suture member securely in the body tissue.

10 Claims, 2 Drawing Sheets

SUTURE AND METHOD OF USE

This application is a continuation-in-part of my application entitled Single Suture Structure, Ser. No. 09/498,308 filed Feb. 4, 2000, now U.S. Pat. No. 6,264,675.

BACKGROUND OF THE INVENTION

1. Field of the Invention

The device of this invention resides in the area of sutures and fasteners for closing the two sides of an incision or cut in human skin or other body tissue and more particularly relates to a suture having adhesive thereon cured by external activation, such suture having an elongated body member with body tissue adhesive thereon which body member is inserted or drawn laterally through a cut to join the two sides of the cut together at which time the adhesive is activated by high-frequency radiation to cause the adhesive to set.

2. Description of the Prior Art

Sutures for closing incisions or wounds are well known in the prior art. Such sutures or ligatures are often attached to the shank end of a needle and are utilized by physicians to make stitches to close incisions or wounds so that they may heal. Frequently such sutures can cause the skin to bunch up in areas where they are tied around the skin rather than bringing the sides of the cut tissue together in neat, parallel alignment. Sutures are formed not only of threadlike material, but are also available as a one-piece unit combined with a needle. Sutures are available in a wide variety of monofilament and braided suture material. Sutures can be formed of non-absorbable material such as cat gut, silk, nylon, polyester, polypropylene, linen, or cotton as well as bioabsorbable synthetic material such as polymers and copolymers of glycolic and lactic acid. Germicides can also be incorporated into the structure of the suture which can be retained by the suture substrate to provide long-lasting germicidal properties.

Also known in the prior art are fasteners which eliminate the need for sutures in many instances. These fasteners are commonly referred to as "staples" and are useful in joining tissue layers laterally, for example, closing wounds in skin or fascia. Such staples are dispensed by implanting devices loaded with such surgical fasteners, the use of which devices can accomplish in very short time what would take many minutes to perform by suturing. Some staples can be made of bioabsorbable materials. The use of such fasteners results in a significant reduction in blood loss and also lowers the level of trauma to the patient. Such staples can be in the form of metal staples which have arms bent by the fastening device to hook the separated body tissue together. Staples can require the stapling apparatus to have an anvil member which must be positioned under the tissue to be stapled so that the arms of the staple can be bent inwards. Two-part fastening devices also have been used which incorporate a barbed staple, the arms of which are attached to a bottom retainer member. In some cases a drawback to employing staples is that a retainer member must be attached under the body tissue to be joined, and one must have access to the body tissue both from above and below the body tissue. Metal staples applied to the body must also be removed by staple extractors.

Other types of surgical fasteners include skin tacks which are used to join two sides of an incision. Such skin tacks include a barbed tip on each end of the inverted U-shaped tack, the body of which is transversely positioned across an incision or cut and the tack is applied so that the barbed tips engage straight downward into the skin to hold each side of the adjacent layers of body tissue together. More recently "zippers" have been applied on each side of an incision which allow for reopening, if desired.

The Applicant herein has patented a suture assembly having a central body member with a plurality of elongated lateral members extending from the central body member from each side thereof, each such lateral member having a plurality of barbs thereon to retain the lateral members securely in the body tissue, as described in U.S. Pat. No. 5,425,747. The Applicant further developed a method of lateral member insertion utilizing shaft-like, removable insertion members which can push each lateral member into position in the tissue and which insertion member can then be removed, as described in Applicant's U.S. Pat. No. 5,584,859. The Applicant also has a pending application Ser. No. 09/498,308 filed Feb. 4, 2000 for a single suture with adhesive thereon which is activatable when drawn into body tissue.

SUMMARY OF THE INVENTION

It is an object of this invention to provide an improved surgical fastener and method for joining skin or other body tissue together such as when separated by a cut or an incision.

The structure of this invention in one embodiment consists of a suture assembly having an elongated body member with first and second ends and having a needle member disposed at one end thereof, a stop member at the other end thereof, and adhesive disposed along the body member. In use one would insert the needle member on the surface of the skin at an entry point adjacent to the cut to be closed on the first side of the cut and draw the suture material, such as a thread member, through the body tissue and out through the first inside of the cut and then into the second inside of the cut and then up through the body tissue of the second side and out an exit point on the surface of the second side of the cut. One would draw the needle member and attached suture/thread member, pulling the suture carrying the adhesive into the body tissue such that the suture is positioned within both sides of the cut. When used, a stop member prevents pulling the suture too far when the suture is stopped from further movement by the stop member's contact with the surface of the skin. One then pulls the sides of the cut together and then activates the adhesive from the exterior of the skin by applying high-frequency radiation onto the skin which radiation passes through the skin and activates and sets the adhesive, thereby retaining the body tissue to the suture and holding the sides of the cut together. The end of the thread member can be cut off once the suture has brought the two sides of the cut together and the suture has been fixed in position by application of high-frequency radiation to set the adhesive. Other types of single sutures can be used such as a suture having a rigid portion for insertion into one side of the cut and a flexible portion which is easily manipulable and pulled by the needle and thread into the other side of the cut after which the cut is closed around the suture and the adhesive on the suture is externally activated, as described above. In some embodiments the suture can include barbs, as described in my prior art inventions, to aid in retaining the body tissue therearound as the suture is positioned for the adhesive to be externally activated. Such improved fastener and joining method can also be used for the fixation of internal tissues such as knee lateral displacement corrections, ligament reattachment operations and the like where an externally activatable and curable adhesive coating on such suture can act as a procedural aid to temporarily hold tissues in tension while the surgeon is performing other acts. The use of the suture of this invention can also be helpful in dental and facial surgery as it eliminates annoying suture knots.

It should be noted that an adhesive can be utilized which, when one frequency of high-frequency radiation is externally applied, will be activated and cured; and when a different frequency radiation is applied to the cured adhesive, will be deactivated, turning the adhesive to a liquid state so that the suture is released from its hold in the tissue. Such liquid adhesive is absorbed by the body. This activation and deactivation of the adhesive is particularly well suited when using temporary suturing as it allows for the reopening of an incision when further work is needed to be done.

DESCRIPTION OF THE PREFERRED EMBODIMENT(S)

Figure 1:
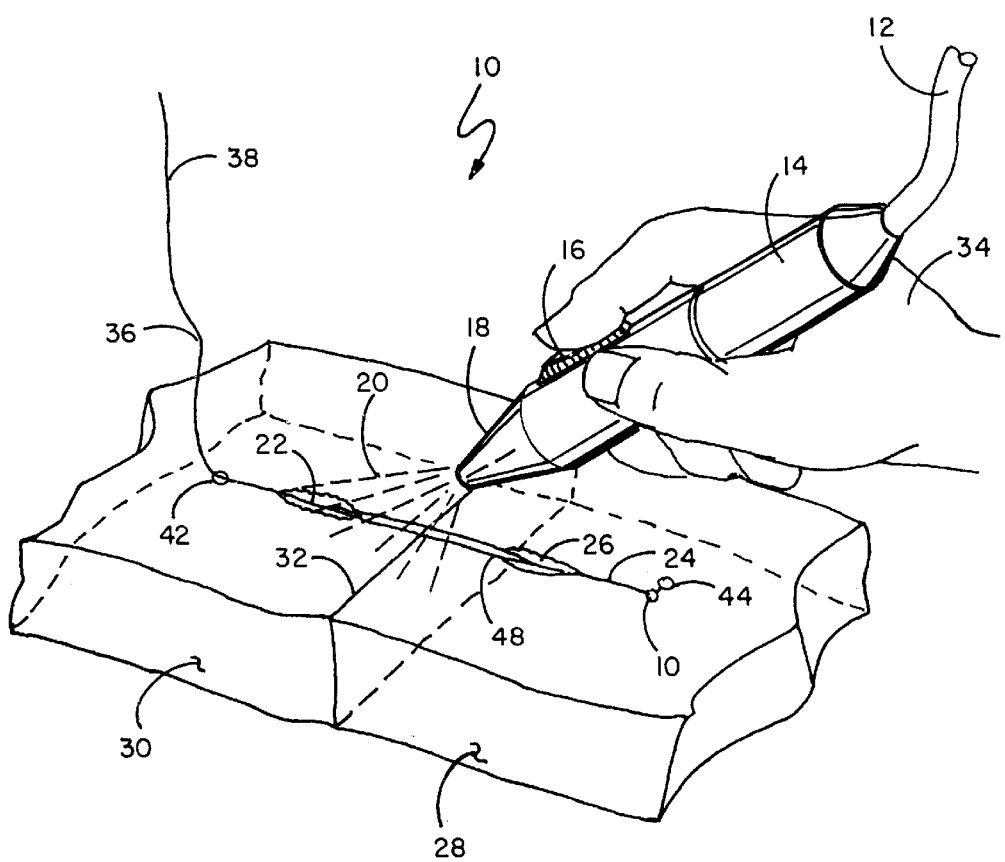
FIG. 1 illustrates a perspective view of the suture and method of use of this invention.

FIG. 1 illustrates a perspective view of suture 10 of this invention which is comprised of elongated body member 24 having first and second ends 48 and 46 on which body member are respectively positioned adhesive segments 22 and 26. Adhesive segments 22 and 26 are activatable by high-frequency radiation waves. Although not necessary, some sutures can have thread member 36 attached at one end to the shank of needle member 38 and at the other end to first end 48 of body member 24. Needle member 38 is entered at insertion point 40 in first side 28 of cut 32 of the body tissue and then drawn through the body tissue and out the first side 28 of cut 32 and into the second side 30 of cut 32. Needle member 38 is then drawn up through the body tissue through exit point 42. One then draws the suture until adhesive segments 22 and 26 are in place on both sides of the tissue and when wide stop member 44 contacts the surface of the skin on first side 28, preventing any further internal movement. In practicing the method of use of this invention, one then directs high-frequency waves 20 from a high-frequency wave generator 14 held in the operator's hand 34. In one method the surgeon can pull the adhesive-coated suture through the wound until the first end of the suture is at a desired position where the surgeon can utilize the high-frequency generator to activate the adhesive at such first end. The surgeon can then pull from the second end of the suture while positioning the tissue and then activate the adhesive with the high-frequency waves at the second end. The operator can turn on and off the high-frequency waves by utilizing on/off switch 16. High-frequency radiation waves 20 can be infrared, ultraviolet, microwaves, laser waves or other types of radiation which pass through the skin or tissue and activate or deactivate the adhesive, thereby bonding suture 10 to the tissue or releasing such bond. The suture member, thread member and adhesive can be made of bioabsorbable materials.

Figure 2:
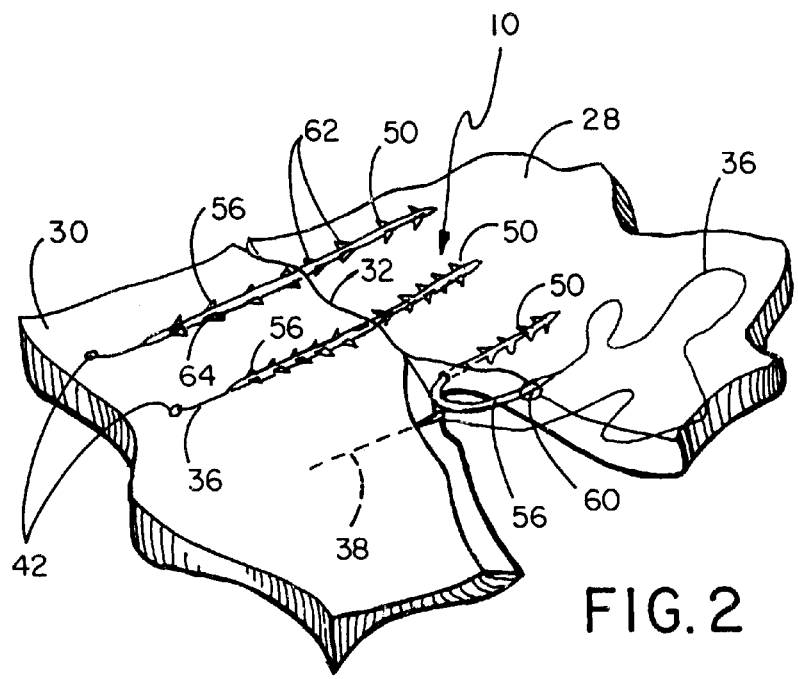
FIG. 2 illustrates a perspective view of an alternate embodiment of the suture of this invention having both a rigid and a flexible component.
Figure 3:
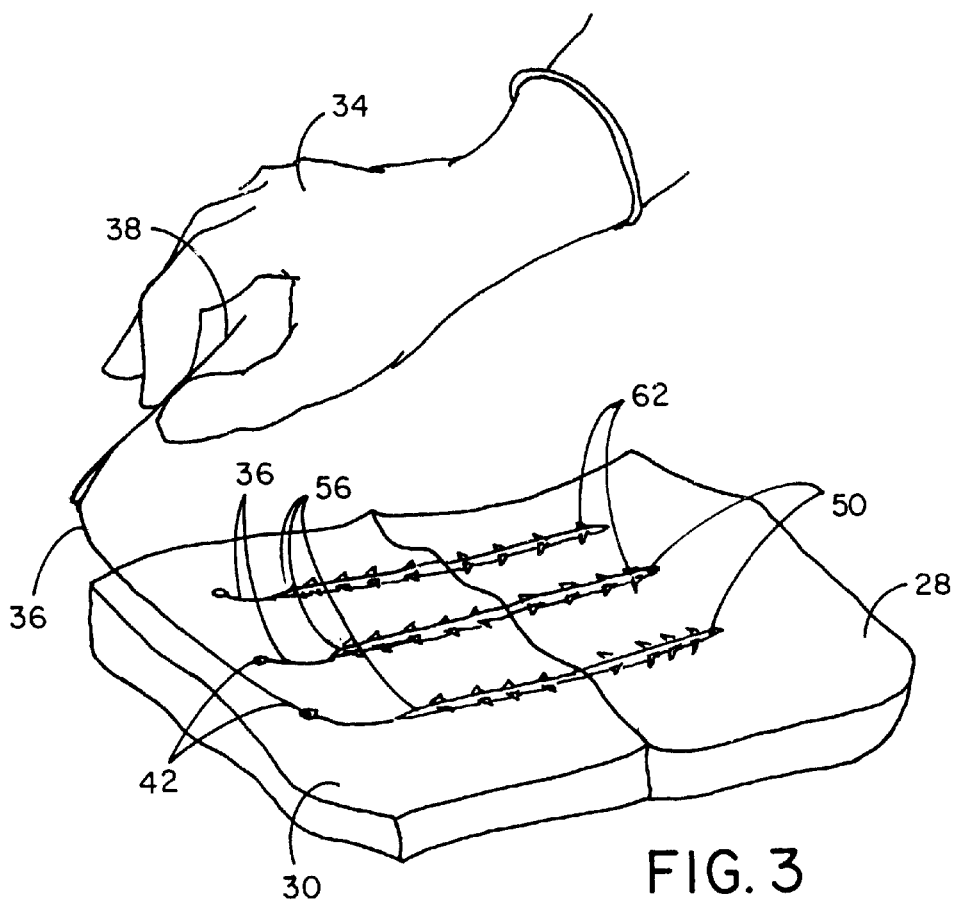
FIG. 3 illustrates the view of FIG. 2 with the suture drawn into position in the cut.

The suture member of this invention can be made of a single piece of material, as illustrated in FIG. 1, or can take the form of other designs of sutures which have adhesive disposed thereon which adhesive is activated by the application of high-frequency radiation in practicing the method of use of this invention. FIG. 2 illustrates another embodiment of the suture of this invention wherein a single suture or multiples of single sutures can be used to join first side 28 and second side 30 of cut 32 together. The suture has rigid portion 50 joined to flexible portion 56. The suture can have a plurality of barbs 62 pointing away from the direction of insertion on each side and adhesive segments 60 thereon. The rigid portion can be a straight, needle-like portion made of body-absorbable plastic that is coated with an externally activatable adhesive. In use, the user can manipulate rigid portion 50 by pushing it into first side 28 of cut 32. Barbs 62 will help hold it in position within the tissue. The user then inserts needle 38 into second side 30 of cut 32 and pulls it out, as seen in FIG. 3, drawing the suture therebehind by thread 36, and the user bends and manipulates flexible portion 56 of the suture to bend and insert it into position within second side 30 of cut 32 so as not to have to manipulate or pull the cut open further than needed. When in position, barbs 62 will help hold cut 32 closed over the suture until the adhesive can be externally activated. In a further embodiment multiple sutures 64 can be used to close cut 32, as seen in FIGS. 2 and 3. One then can use a high-frequency wave generator, such as seen in FIG. 1, to activate adhesive segments 60. The use of parallel sutures of this invention avoids the need for traditional stitches, thus avoiding prior art loop and knot suturing which tightens and constricts the tissue that it encompasses which prior art suturing causes face-to-face cut surface symmetry to be lost. The present invention, on the other hand, allows the sides of the cut, wound or incision to be brought together in striate parallel fashion and provides better wound healing. The parallel joining of tissue according to the method of this invention provides an improved inflammatory reduction response and better blood clotting fibrin strand shrinkage and easier debris removal. New capillary growth is encouraged due to the improved joining of the sides of the cut by the suture and method of this invention, thereby avoiding large collagen formations and thus reducing scarring.

The ligature materials for the sutures of this invention can be made of commercial material and synthetic absorbable suture materials such as gut, reconstituted collagen, polyglycolide or equivalent. The sutures can also be of non-absorbable materials such as silk, cotton, linen, polyester, polyamide, polypropylene, polytetrafluoroethylene, stainless steel or equivalent material. The externally activated adhesives can be made of any materials that will exhibit an adhesive quality upon exposure to high-frequency radiation such as materials from the polymerizable groups, such as acrylamide, methacrylamide, itaconate and styrene groups. Such materials are known biological adhesives that become active when exposed to ultraviolet light or other high-frequency waves. Many of such externally activatable adhesives are bioresorbable and polymerize upon exposure to specific wavelengths and/or heat.

Although the present invention has been described with reference to particular embodiments, it will be apparent to those skilled in the art that variations and modifications can be substituted therefor without departing from the principles and spirit of the invention.

I claim:

1. A suture for joining the first and second sides of a cut defined in body tissue, comprising:

an elongated body member having first and second ends for insertion, respectively, in said first and second sides of said cut; and externally activatable adhesive material disposed on said body member, said adhesive material to be activated by application of high-frequency radiation after being drawn into and positioned in said first and second sides of said cut in said body tissue.

2. The suture of claim 2 wherein said adhesive material is selectively deactivatable by application of high-frequency radiation.

3. The suture of claim 1 further including a needle member and thread disposed at said second end of said body member.

4. The suture of claim 3 further including a stop member disposed at said first end of said body member.

5. The suture of claim 1 wherein said body member is composed of a rigid portion and a flexible portion.

6. The suture of claim 1 further including a plurality of barbs disposed on said body member.

7. The suture of claim 5 further including a plurality of barbs disposed on said body member.

8. A method of joining together the first and second sides of a cut defined in body tissue, comprising the steps of:

providing a suture member having first and second ends, said suture member having adhesive material disposed thereon, said adhesive material activatable by high-frequency radiation;

inserting said first and second ends of said suture member respectively in said first and second sides of said cut;

closing said first and second sides of said cut;

externally applying selected ranges of high-frequency radiation through said body tissue to said adhesive material on said suture member;

activating and setting said adhesive material; and joining said first and second sides of said cut together by said suture.

9. The method of claim 8 further including the step of:

inserting multiple suture members substantially parallel to one another and generally perpendicular to said cut.

10. The method of claim 8 further including the steps of:

deactivating and unsetting selected portions of said adhesive material by applying of high-frequency radiation from selected ranges thereof to said selected portions of said adhesive material; and unjoining said tissue from said suture.

* * * * *